United States Patent [19]

Koszyk et al.

[11] Patent Number: 4,876,268

[45] Date of Patent: Oct. 24, 1989

[54] ANTIVIRAL COMPOUNDS AND USE THEREOF

[75] Inventors: Francis J. Koszyk, Chicago; Richard A. Partis, Evanston; Richard A. Mueller, Glencoe, all of Ill.

[73] Assignee: G. D. Searle & Co., Skokie, Ill.

[21] Appl. No.: 266,718

[22] Filed: Nov. 3, 1988

[51] Int. Cl.$^4$ .................... C07D 207/12; A61K 31/40
[52] U.S. Cl. ..................................... 514/425; 548/556
[58] Field of Search ......................... 514/425; 548/556

[56] References Cited

U.S. PATENT DOCUMENTS

| | | | |
|---|---|---|---|
| 3,312,716 | 4/1967 | Biel et al. | 548/556 |
| 4,182,767 | 1/1980 | Murai et al. | 424/267 |
| 4,639,436 | 1/1987 | Junge et al. | 514/24 |

FOREIGN PATENT DOCUMENTS 8703903  7/1987  PCT Int'l Appl. .

OTHER PUBLICATIONS

Frank, Antimicrob. Agents Chemother. 31, 1369–1374, (1987).
Sunkara et al., Soc. Complex Carbohyd., 17th Ann. Meet., San Antonio, Nov. 3–5, 1988, Abstract 9.

*Primary Examiner*—David B. Springer
*Attorney, Agent, or Firm*—Scott J. Meyer; James W. Williams, Jr.

[57] ABSTRACT

Acylated derivatives of 1,4-dideoxy-1,4-imino-L-arabinitol and their N-alkyl and N-hydroxyalkyl derivatives in which all the free hydroxyl groups are acylated with acyl groups having from one to six carbon atoms and in which the N-alkyl substituents in the N-alkyl and N-hydroxyalkyl derivatives contain from one to fourteen carbon atoms are disclosed.

5 Claims, No Drawings

ANTIVIRAL COMPOUNDS AND USE THEREOF

BACKGROUND OF THE INVENTION

This invention relates to novel antiviral compounds and, more particularly, to acylated derivatives of 1,4-dideoxy-1,4-imino-L-arabinitol and their N-alkyl and N-hydroxyalkyl derivatives. These compounds are inhibitors of visna virus, and, as such, have potential use for the treatment of acquired immune deficiency syndrome (AIDS).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4+ T-cells (or CD4+ cells). See, e.g., Gallo et al., Science 224, 500–503 (1984), and Popovic et al., Ibid., 497–500 (1984). This retrovirus has been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [*Ann. Virol. Inst. Pasteur* 135 E, 119–134 (1984)], while HIV-2 was more clearly isolated by Montagnier and his coworkers in 1986 [*Nature* 326, 662 (1987)]. As used herein, HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, *Science* 241, 426–432 (1988).

The first drug to be approved by the U.S. Food and Drug Administration (FDA) for treatment of AIDS was zidovudine, better known under its former name azidothymidine (AZT). Chemically, this drug is 3'-azido-3'-deoxythymidine. This drug was originally selected as a potential weapon against AIDS because it was shown to inhibit replication of the virus in vitro. Such in vitro tests are useful and virtually the only practical method of initially screening and testing potential anti-AIDS drugs. A serious drawback of AZT, however, is its toxic side-effects. Thus, the search for better anti-AIDS drugs continues.

The HIV inhibitory activity of 1,4-dideoxy-1,4-imino-L-arabinitol and its N-methyl derivative is disclosed in copending application Ser. No. 249,144, filed Sept. 26, 1988.

BRIEF DESCRIPTION OF THE INVENTION

In accordance with the present invention acylated derivatives of 1,4-dideoxy-1,4-imino-L-arabinitol and their N-alkyl and N-hydroxyalkyl derivatives have been found to have useful antiviral activity.

1,4-dideoxy-1,4-imino-L-arabinitol is a five-membered heterocyclic compound having nitrogen in the ring and 3 hydroxyl groups. It is thus described by a systemic chemical name as a sugar derivative in which the five-membered ring is considered as a mimic of furanose, with nitrogen instead of oxygen in the ring. It can also be described structurally as a derivative of pyrrolidine. As defined herein, all the free hydroxyl groups on the 1,4-dideoxy-1,4-imino-L-arabinitol and the N-substituted derivatives are acylated with acyl groups having from one to six carbon atoms. These compounds thus will contain from 3 to 4 such acyl substituents. A preferred acyl group is an alkyanoyl such as acetyl. In the N-alkyl and N-hydroxyalkyl derivatives, the N-alkyl substituents contaim from 1 to 14 carbon atoms.

Preferred antiviral compounds of this invention are triacetate and tetraacetate derivatives exemplified as follows:

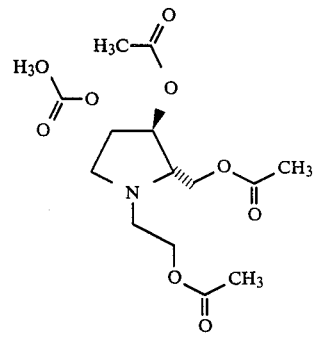

1,4-[[2-(acetyloxy)ethyl]iminol-1,4-dideoxy-L-arabinitol, triacetate

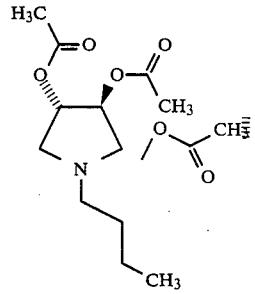

1,4-(butylimino)-1,4-dideoxy-L-arabinitol, triacetate

The foregoing compounds have been found to have inhibitory activity against visna virus in a conventional plaque reduction assay. Inhibition of visna virus replication in vitro as a useful model for human immunodeficiency virus (HIV) and its inhibition by test compounds has been described by Frank et al., *Antimicrobial Agents and Chemotherapy* 31 (9), 1369–1374 (1987). The N-butyl derivative of 1,5-dideoxy-1,5-imino-D-glucitol, also referred to as N-butyl-deoxynojirimycin (N-Bu-DNJ), was used as a control standard for comparison with the novel compounds of this invention. The HIV inhibitory activity of N-Bu-DNJ is described in copending application Ser. No. 248,461, filed Sept. 23, 1988.

DETAILED DESCRIPTION OF THE INVENTION

The following detailed examples will further illustrate the invention although it will be understood that the invention is not limited to these specific examples.

EXAMPLE 1

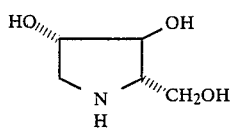

1,4-Dideoxy-1,4-imino-L-arabinitol

The title compound was prepared by the method described by Fleet and Smith, *Tetrahedron* 42, 5685–5692 (1986), the disclosure of which is incorporated herein by reference.

EXAMPLE 2

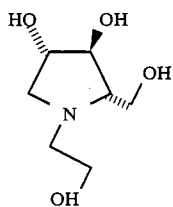

1,4-dideoxy-1,4-[2-hydroxyethyl)imino)-L-arabinitol

To a solution of the title product of Example 1 (1.44 g, 8.50 moles) in 25 ml of methanol was added a solution of sodium bicarbonate (714 mg, 8.50 moles) in 10 ml of water. After stirring for a few minutes, the solvent was removed on a rotary evaporator. The residue was then dissolved in anhydrous ethanol, and the solvent was removed on a rotary evaporator. The residue was dissolved in a mixture of 29 ml of methanol and 1.5 ml of acetic acid. The the resulting mixture was added glycolaldehyde dimer (1.02 g, 8.50 moles), 5 g of 4A molecular sieves, and then, in portions, sodium cyanoborohydride (553 mg, 8.81 moles). After stirring overnight at room temperature, the mixture was filtered, and the solvent was removed on a rotary evaporator. Chromatography of the residue on silica gel using 50-50 ethyl acetate-methanol as eluant gave the title compound (1.82 g) as an oil. The compound was identified by proton and carbon NMR spectrometry.

EXAMPLE 3

C15 H23 N 08
345.352

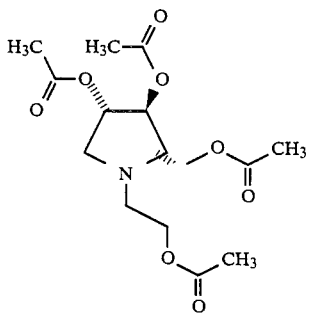

1,4-[[2-(acetyloxy)ethylliminol-1,4-dideoxy-L-arabinitol, triacetate

To a solution of the title product of Example 2 (343 mg, 1.9 moles) in 10 ml of pyridine was added 4 ml of acetic anhydride. The residue was stirred for one hour at room temperature, and then at reflux for 5 minutes. After cooling, the mixture was poured into 30 ml of ice water and extracted with three portions of ethyl acetate. The combined organic extracts were washed with 25 ml of dilute hydrochloric acid, dried over sodium sulfate, filtered, and the solvent removed on a rotary evaporator. Chromatography of the residue over silica gel using a gradient of 50 to 75% ethyl acetate-hexane as eluant gave the title compound (418 mg) as an oil.

Analysis for $C_{15}H_{23}NO_8$: (MW 345.35): Calcd.: C, 52.17; H, 6.71; N, 4.06. Found: C, 51.77; H, 6.66; N, 4.00.

EXAMPLE 4

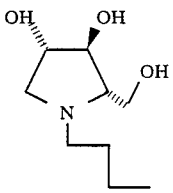

1,4-(butylimino)-1,4-dideoxy-L-arabinitol

The title compound (822 mg) was prepared as an oil by the method of Example 3 by using N-butyraldehyde (1.27 g) instead of glycolaldehyde dimer, and by using 1.50 g of the product of Example 1. The title compound was identified by proton and carbon NMR spectrometry.

EXAMPLE 5

C15 H25 N 06
315.37

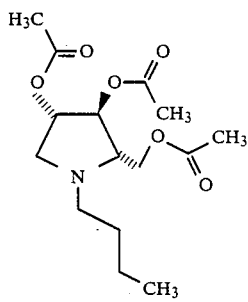

1,4-(butylimino)-1,4-dideoxy-L-arabinitol, triacetate

The title compound (418 mg) was prepared as an oil by the method of Example 3, using the product of Example 4 instead of the product of Example 2 as the starting material, and using 35% ethyl acetatehexane as the chromatography eluent.

Analysis for $C_{15}H_{25}NO_6$: (MW 315.37): Calcd.: C, 57.13; H, 7.99; N, 4.44. Found: C, 56.84; N, 7.85; N, 4.42.

EXAMPLE 6

The preferred compounds of this invention were tested for inhibition of visna virus in vitro in a plaque reduction assay as follows:

METHOD

Cell and virus propagation

Sheep choroid plexus (SCP) cells were obtained from American Type Culture Collection (ATCC) catalogue number CRL 1700 and were routinely passaged in vitro in Dulbecco's Modified Eagles (DME) medium supplemented with 20% fetal bovine serum (FBS). SCP cells were passaged once per week at a 1:2 or 1:3 split ratio. Visna was titrated by plaque assay in six-well plates. Virus pools were stored at −70° C.

Plaque reduction assay

SCP cells were cultured in 6-well plates to confluence. Wells were washed two times with serum free Minimal Essential Medium (MEM) to remove FBS. 0.2 ml of virus was added per well in MEM supplemented with 4 mM glutamine and gentamycin. After 1 hour adsorption, the virus was aspirated from each well. The appropriate concentration of each compound in 5ml of Medium 199 (M-199) supplemented with 2% lamb serum, 4 mM glutamine, 0.5% agarose and gentamycin was added to each well. Cultures were incubated at 37° C. in a humidified 5% $CO_2$ incubator for 3-4 weeks. To terminate the test: cultures were fixed in 10% formalin, the agar removed, the monolayers stained with 1% crystal violet and plaques counted. Each compound concentration was run in triplicate. Control wells (without virus) were observed for toxicity of compounds at the termination of each test and graded morphologically from 0 to 4. 0 is no toxicity observed while 4 is total lysing of the cell monolayer.

96 well plate assay

The 96 well plate assay was performed similarly to the plaque assay above with modifications. SCP cells were seeded at 1×10⁴ cells per well in 0.1 ml DME medium. When confluent, the wells were washed with serum free MEM and 25 μl of virus added in M-199 supplemented with 2% lamb serum. After 1 hour, 75 μL of medium containing test compound was added to each well containing virus. After 2-3 weeks incubation the cytopathic effect of the virus was determined by staining with a vital stain. Cell viability was measured by determining stain density using a 96 well plate reader.

Control wells without virus were completed to determine the toxicity of compounds.

RESULTS

Table 1, below, sets forth the results of the assay for the compounds of Examples 3 and 5 compared to the N-butyl derivative of 1,5-dideoxy-1,5-imino-D-glucitol (N-Bu-DNJ) as a control standard.

TABLE 1

| Compound Example No. | PLAQUE REDUCTION ASSAY | | | |
|---|---|---|---|---|
| | Concentration mM | Toxicity | % Plaque Reduction | Antiviral Activity |
| N—Bu—DNJ | 1.0 | 2 | 100 | A |
| | 0.1 | 1 | 100 | A |
| | 0.01 | 0 | 13 | I |
| | 0.001 | 0 | 74 | I |
| 3 | 1.0 | 0 | 90 | A |
| | 0.1 | 0 | 72 | A |
| | 0.01 | 0 | −64 | I |
| | 0.001 | 0 | −46 | I |
| 5 | 1.0 | 0 | 83 | A |
| | 0.1 | 0 | 10 | I |
| | 0.01 | 0 | 10 | I |
| | 0.001 | 0 | 9 | I |

A = active compound; I = inactive
Toxicity graded on 0 to 4 scale; 0 = no toxicity and 4 = total cell lyses.
N—Bu—DNJ = n-butyl-deoxynojirimycin used as a control standard.

The antiviral agents described herein can be used for administration to patients infected with a virus, e.g. the human immunodeficiency virus, by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences,* Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such other examples be included within the scope of the appended claims.

What is claimed is:

1. Acylated derivatives of 1,4-dideoxy-1,4-imino-L-arabinitol and their N-alkyl and N-hydroxyalkyl derivatives in which all the free hydroxyl groups are acylated with acyl groups having from one to six carbon atoms and in which the N-alkyl substituents in the N-alkyl and N-hydroxyalkyl derivatives contain from one to fourteen carbon atoms.

2. The acylated derivatives of claim 1 in which the acyl groups are acetyl.

3. 1,4-[(2-(acetyloxyethyl)-imino]-1,4-dideoxy-L-arabinitol, triacetate.

4. 1,4-(butylimino)-1,4-dideoxy-L-arabinitol, triacetate.

5. The method of inhibiting virus by treating a patient with a virally inhibitory effective amount of an acylated derivative of claim 1.

* * * * *

UNITED STATES PATENT AND TRADEMARK OFFICE
CERTIFICATE OF CORRECTION

PATENT NO. : 4,876,268

DATED : Oct. 24, 1989

INVENTOR(S) : Francis J. Koszyk, Richard A. Partis, and Richard A. Mueller

It is certified that error appears in the above—identified patent and that said Letters Patent is hereby corrected as shown below:

At col. 4, line 34, "Example 3" should read —Example 2—. In the structural chemical formulas at col. 2, lines 23 and 41, bond lines should be inserted in the blank spaces between the pyrrolidine ring structure and the adjacent, dangling substituent to show bonds as in identical formulas at col. 3, line 58 and col. 4, line 52, respectively.

Signed and Sealed this

Second Day of October, 1990

Attest:

HARRY F. MANBECK, JR.

*Attesting Officer*     *Commissioner of Patents and Trademarks*